United States Patent
Crosswell, Jr.

(10) Patent No.: US 8,206,362 B1
(45) Date of Patent: Jun. 26, 2012

(54) DEVICE FOR ADMINISTERING EYE DROPS

(75) Inventor: Hal H. Crosswell, Jr., Columbia, SC (US)

(73) Assignee: E-Z Eye Med, Inc., Lugoff, SC (US)

( * ) Notice: Subject to any disclaimer, the term of this patent is extended or adjusted under 35 U.S.C. 154(b) by 458 days.

(21) Appl. No.: 11/242,644

(22) Filed: Oct. 3, 2005

Related U.S. Application Data

(60) Provisional application No. 60/615,128, filed on Oct. 1, 2004.

(51) Int. Cl.
*A61M 35/00* (2006.01)
(52) U.S. Cl. ........ 604/294; 604/289; 604/290; 604/291; 604/292; 604/293; 604/295; 604/296; 604/297; 604/298; 604/299; 604/300; 604/301; 604/302; 222/212; 222/420; 222/421; 222/422
(58) Field of Classification Search ........... 604/290–302
See application file for complete search history.

(56) References Cited

U.S. PATENT DOCUMENTS

| | | | |
|---|---|---|---|
| 2,676,592 A | 4/1954 | Wood | |
| 3,058,466 A | 10/1962 | Routsong | |
| 3,934,590 A | 1/1976 | Campagna et al. | |
| 4,134,403 A | 1/1979 | Johnsen et al. | |
| 4,257,417 A | 3/1981 | Gibilisco | |
| 4,531,944 A * | 7/1985 | Bechtle | 604/302 |
| 5,255,024 A * | 10/1993 | Jensen | 351/158 |
| 5,387,202 A * | 2/1995 | Baron | 604/300 |
| 5,578,021 A * | 11/1996 | Cornish | 604/300 |
| 5,713,495 A | 2/1998 | Menard | |
| 6,010,488 A * | 1/2000 | Deas | 604/295 |
| 6,595,970 B1 | 7/2003 | Davidian | |

* cited by examiner

*Primary Examiner* — Tatyana Zalukaeva
*Assistant Examiner* — Ilya Treyger
(74) *Attorney, Agent, or Firm* — Nelson Mullins Riley & Scarborough LLP

(57) ABSTRACT

The present invention provides a device to facilitate the self-administration of eye drops. The device includes a body portion adapted for placement on the user's face, generally over the eye in which the drops are to be applied. The body portion preferably includes an integral handle which may be held between the thumb and forefinger of the user. Many embodiments may also incorporate a nose bridge to assist in locating the device in the correct position.

7 Claims, 8 Drawing Sheets

DEVICE FOR ADMINISTERING EYE DROPS

PRIORITY CLAIM

This application claims the benefit of provisional application Ser. No. 60/615,128, filed Oct. 1, 2004, which is relied upon and incorporated herein by reference.

BACKGROUND OF THE INVENTION

The present invention generally relates to an apparatus for the self-administration of eye drops.

Many people have difficulty administering eye drops in their own eyes. According to the typical process, a user first attempts to position the eye drop bottle at the correct location above their eye. While holding the bottle in this location, the user squeezes the bottle in an effort to cause the correct number of drops to be released. The drops fall, hopefully into the user's open eye below.

While this process works as intended much of the time, often it does not. For example, some users, particularly those who are elderly or otherwise lacking sufficient dexterity, may have difficulty holding the bottle in the correct position relative to the eye. This may result in substantial waste, i.e., drops running down the user's face. When this happens, the bottle of drops may not last as long as intended, requiring the user to refill the prescription more often. For people on fixed incomes, this can cause a substantial financial burden.

There exists a need for a device that facilitates the self-administration of eye drops, leading to less waste and more accurate application.

SUMMARY OF THE INVENTION

The present invention provides a device to facilitate the self-administration of eye drops. The device includes a body portion adapted for placement on the user's face, generally over the eye in which the drops are to be applied. The body portion preferably includes an integral handle which may be held between the thumb and forefinger of the user. Many embodiments may also incorporate a nose bridge to assist in locating the device in the correct position.

The device preferably includes an aperture for receiving the tip portion of the eye drop bottle. Preferably, the aperture may be equipped with flexible fingers or the like to frictionally engage this portion of the bottle in order to hold it in place. The aperture is sized and positioned such that the tip portion of the eye drop bottle will be located in the ideal position with respect to the user's eye when the device is correctly positioned on the user's face.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings, in which.

Figure 1:
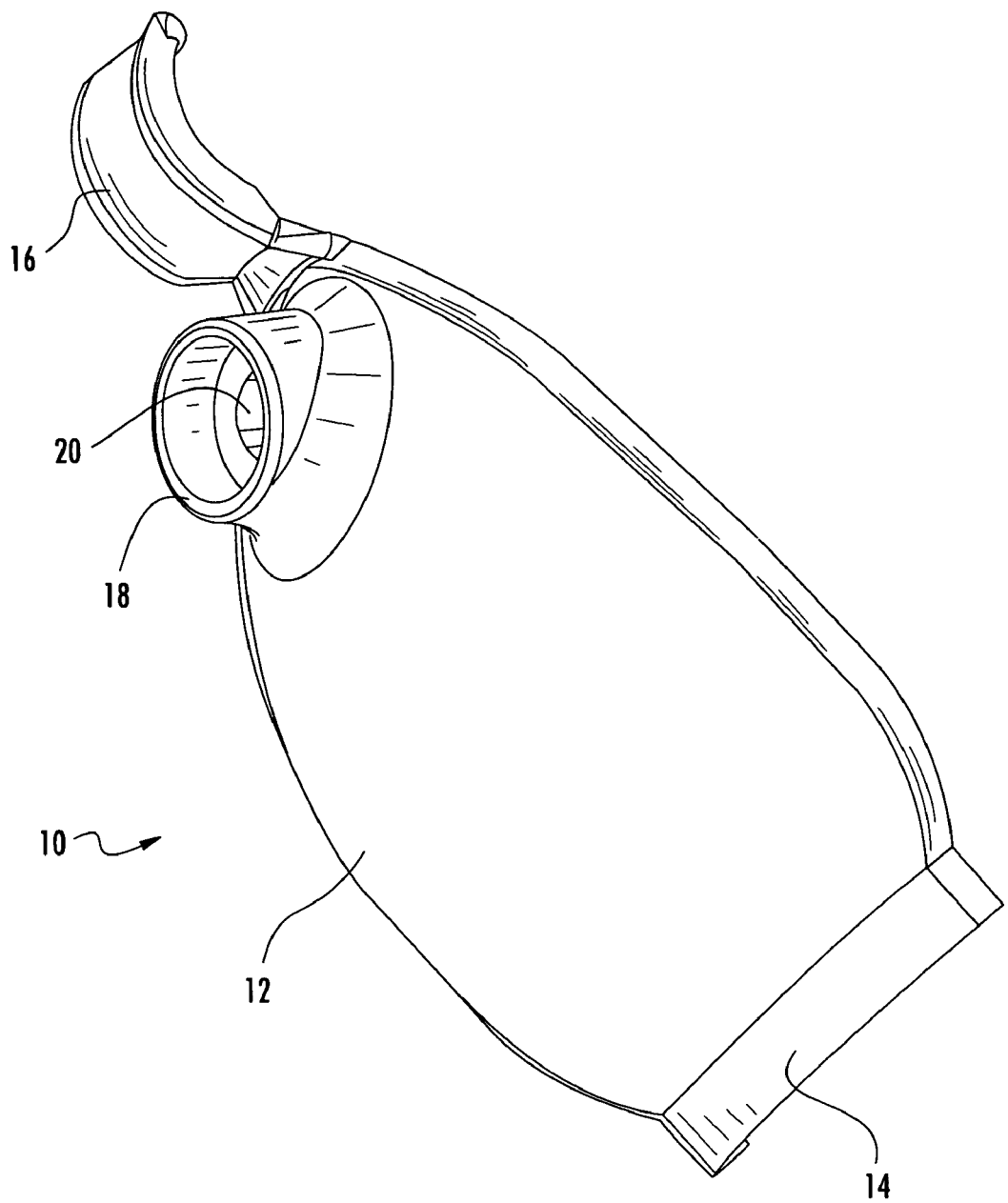
FIG. 1 is a perspective view of a first embodiment of a device constructed in accordance with the present invention.
Figure 2:
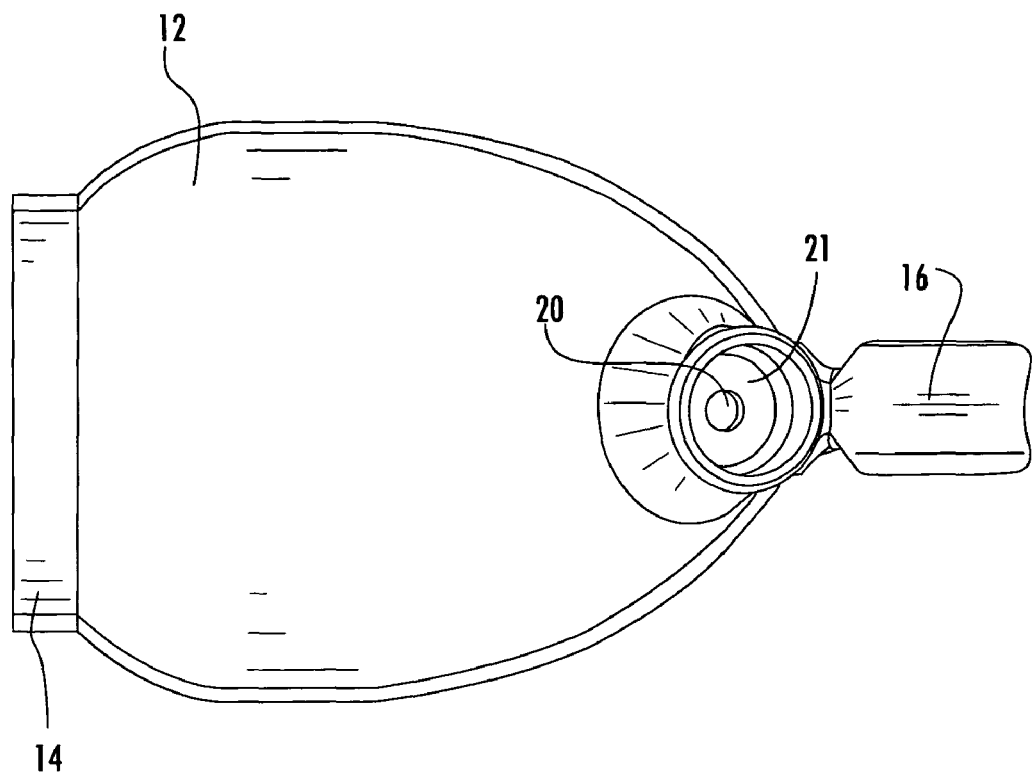
FIG. 2 is a top view of the device illustrated in FIG. 1.

Repeat use of reference characters in the present specification and drawings is intended to represent same or analogous features or elements of the invention.

DETAILED DESCRIPTION OF EXEMPLARY EMBODIMENTS

It is to be understood by one of ordinary skill in the art that the present discussion is a description of exemplary embodiments only and is not intended as limiting the broader aspects of the present invention, which broader aspects are embodied in the exemplary constructions.

Referring now to FIG. 1, a device 10 in accordance with the present invention includes a body portion 12 which is located generally over the eye in which the drops are to be placed. Body portion 12 includes an integral handle 14 which may be held between the thumb and forefinger of the user.

In this case, a nose bridge 16 is provided to assist in locating the device in the correct position. Nose bridge 16 is configured in this embodiment as an arcuate member integrally extending from body portion 12. Specifically, the proximate end of nose bridge 16 is attached to body portion 12 adjacent to raised structure 18. The distal end of nose bridge 16 is spaced from body portion 12 as shown.

A raised structure 18 is configured to receive the tip portion of the eye drop bottle. In particular, structure 18 includes an aperture 20 through which the tip of the bottle extends. Aperture 20 may be provided with flexible fingers or the like which tend to frictionally engage this portion of the bottle in order to hold it in place. For example, the illustrated embodiment utilizes a flexible web 21 defining a central aperture through which the tip is received. Structure 18 and aperture 20 are sized and positioned such that the tip of the eye drop bottle will be located in the ideal position with respect to the user's eye when the device is correctly positioned on the face.

Figure 3:
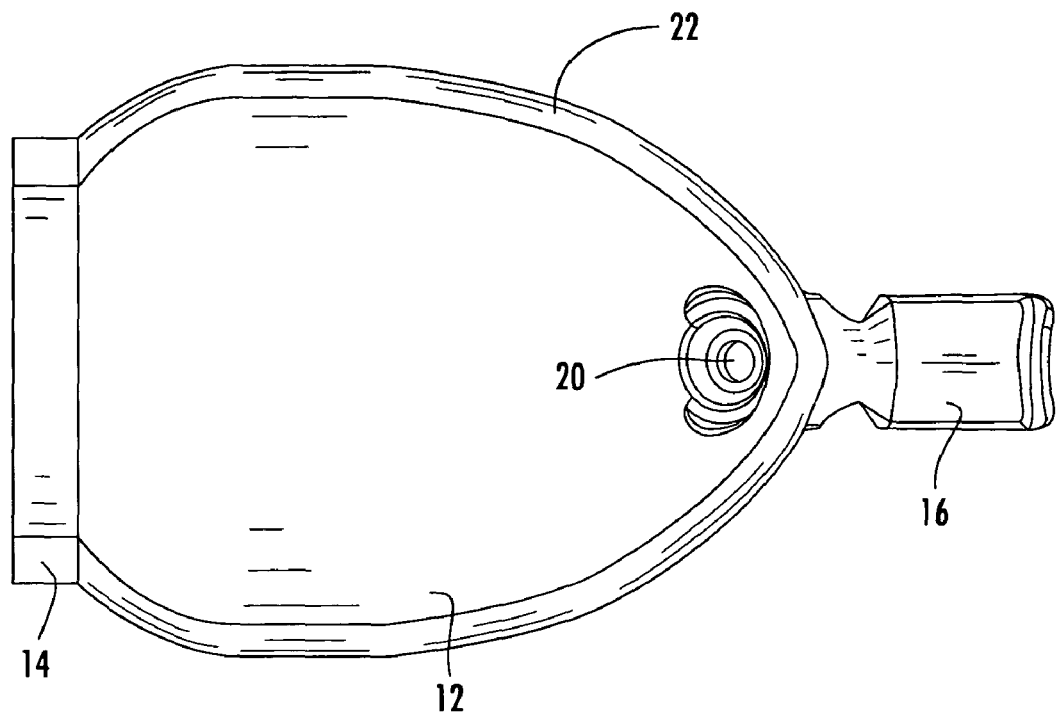
FIG. 3 is a bottom view of the device illustrated in FIG. 1.
Figure 4:
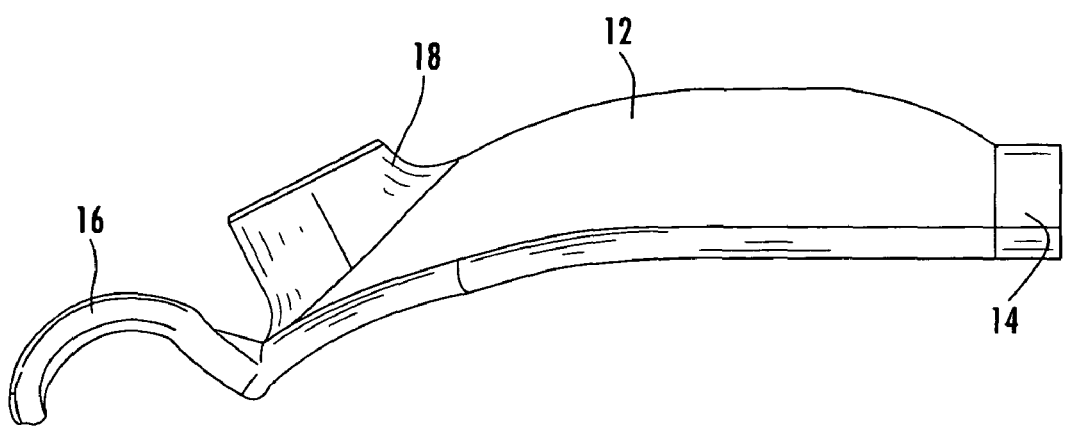
FIG. 4 is a side view of the device illustrated in FIG. 1.
Figure 5:
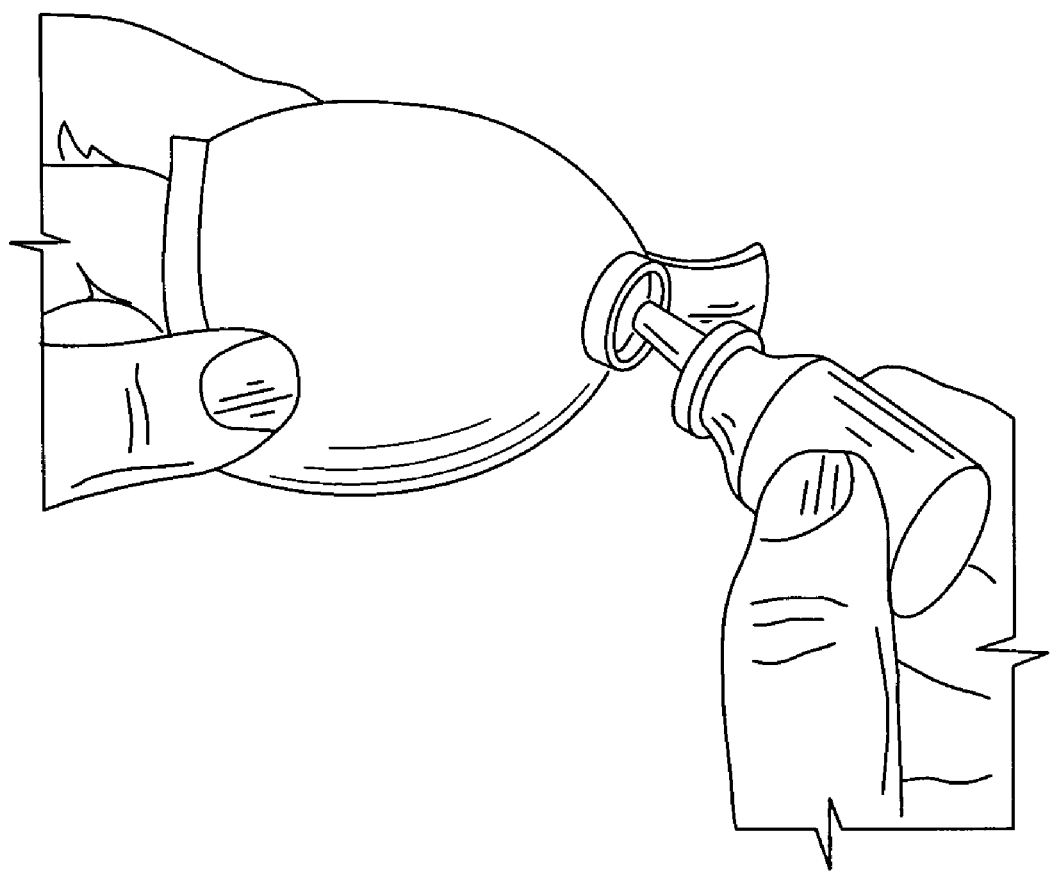
FIG. 5 shows one step in use of the device.
Figure 6:
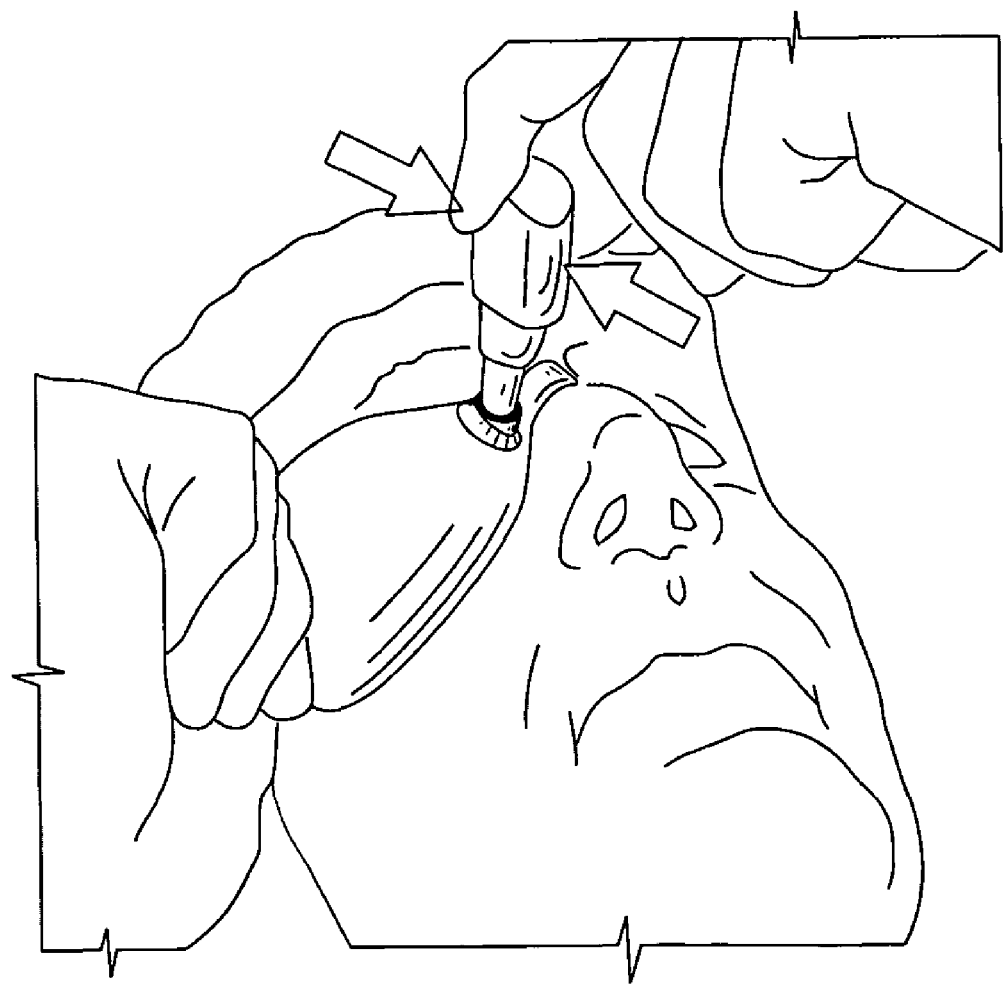
FIG. 6 shows another step in use of the device.
Figure 7:
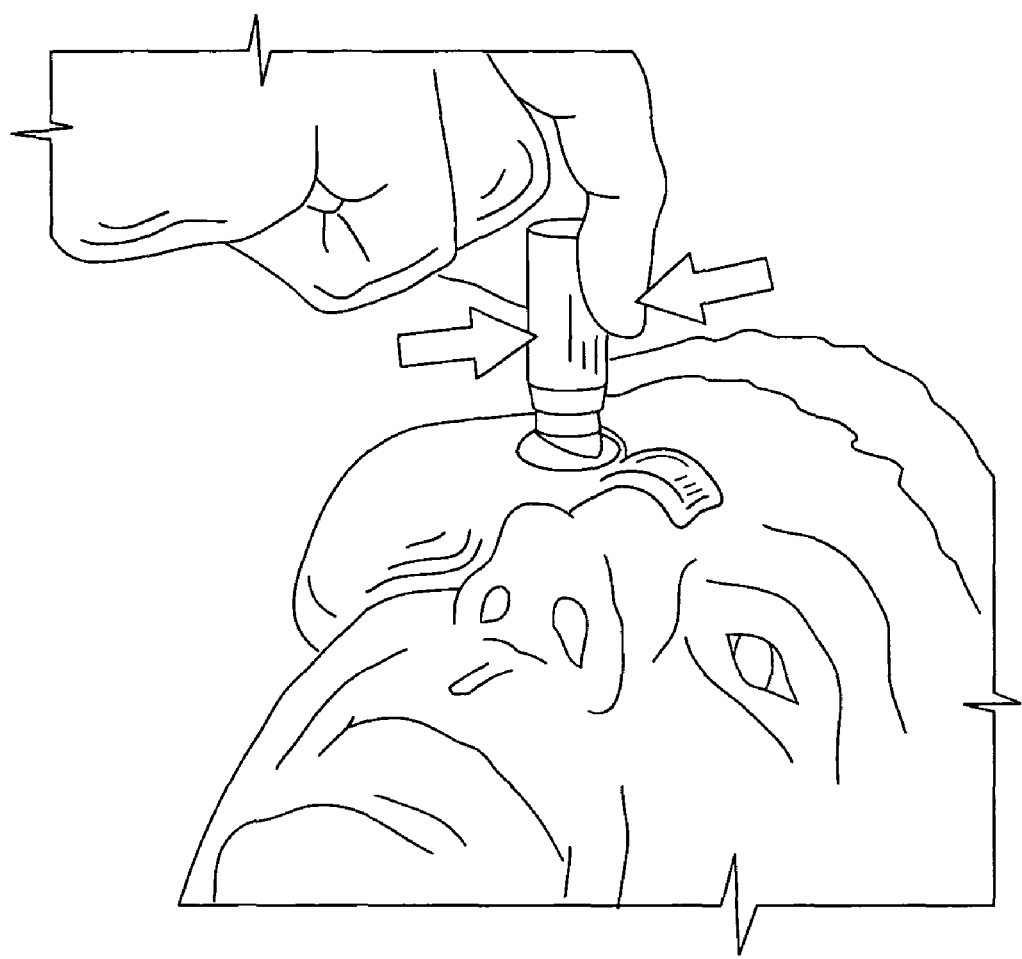
FIG. 7 shows another step in use of the device.

FIGS. 5-7 illustrate certain steps in use of the device. As shown in FIG. 5, the cap of the medication bottle is removed and the tip of the bottle is inserted through the aperture. Referring now to FIG. 6, drops can be placed in the eye by either tilting the head backwards or lying flat on one's back. The device is then placed in the proper position and drops are squeezed into the eye. As can be seen, body portion 12 will substantially cover the eye into which the drops are to be applied. In this regard, the perimeter of body portion 12 may include a rounded edge 22 (FIG. 3) to enhance user comfort. Edge 22, as shown, will engage the user's face adjacent to and around the user's eye. One skilled in the art will note that handle 14 forms a discontinuity in edge 22.

FIG. 7 illustrates how the device can be effectively operated with one hand. This is because the medication bottle will remain attached to the device after its tip portion is inserted into aperture 20. The user can therefore position the combination by grasping the bottle itself. After the medication is applied, the user can separate the bottle and device and then place the cap back on the bottle.

Figure 8:
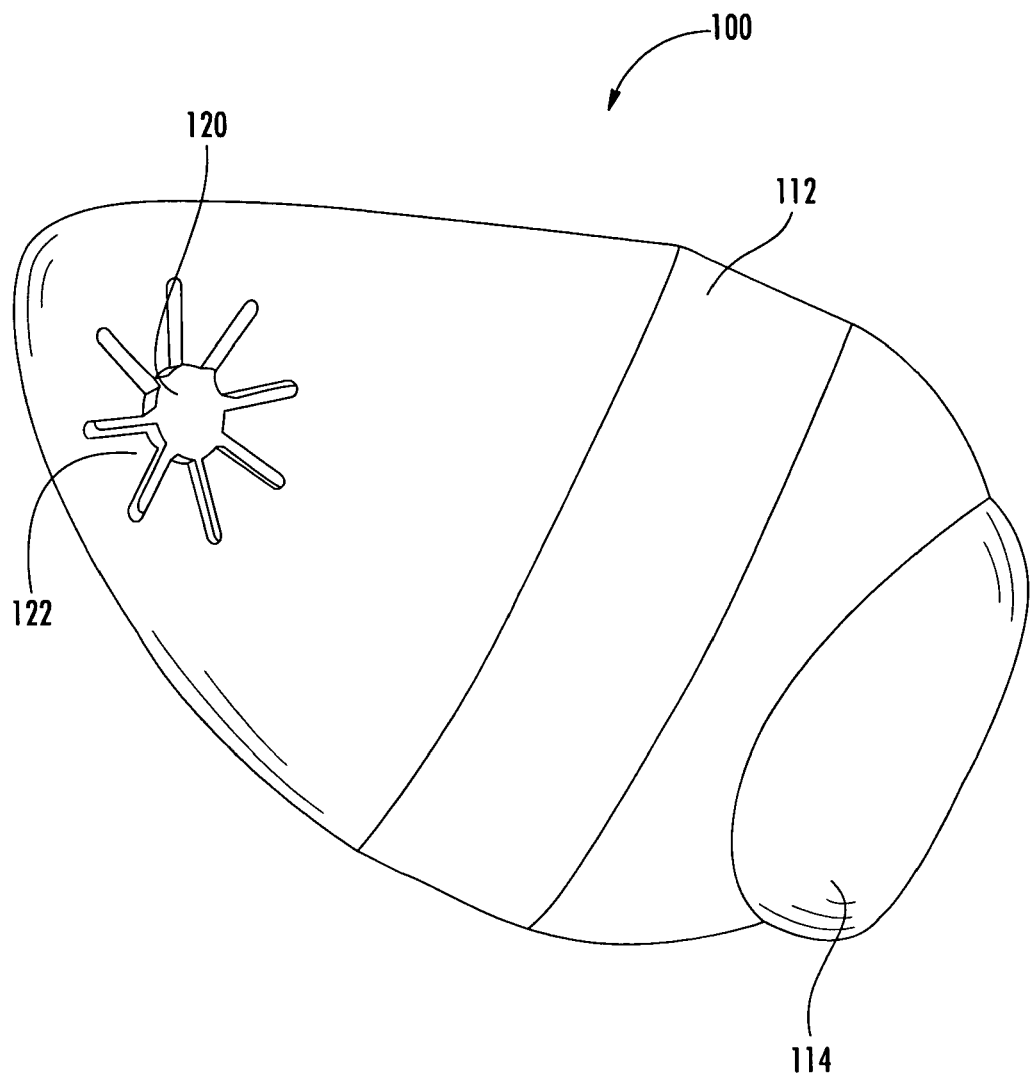
FIG. 8 is a perspective view of another embodiment of a device constructed in accordance with the present invention.

FIG. 8 illustrates a device 100 in accordance with a second embodiment of the present invention. Device 100 includes a body portion 112 which is located generally over the eye in which the drops are to be placed. Body portion 112 includes an integral handle 114 which may be held between the thumb and forefinger of the user. It can be seen that this embodiment does not employ a nose bridge.

An aperture 120 through which the tip of the bottle extends is defined in body portion 112. In this case, aperture 120 has flexible fingers 122 to frictionally engage the tip portion of the bottle. As with the embodiment above, aperture 120 is sized and positioned such that the tip of the eye drop bottle will be located in the ideal position with respect to the user's eye when the device is correctly positioned on the face.

Preferably, a device in accordance with the present invention may be made of a suitable semi-rigid polymeric material. A material having a soft hand feel is especially preferred to enhance user comfort.

While preferred embodiments of the invention have been shown and described, modifications and variations may by made thereto by those of skill in the art without departing from the spirit and scope of the present invention. It should also be understood that aspects of various embodiments may be interchangeable in whole or in part. Furthermore, those of ordinary skill in the art will appreciate that the foregoing description is by way of example only, and is not intended to be limitative of the invention described herein.

What is claimed is:

1. A device to facilitate the self-administration by a user of eye drops from an eye drop bottle, said device comprising:
 a body portion adapted for placement on the user's face at a location over the eye in which the drops are to be applied, said body portion having a peripheral edge adapted to engage the user's face adjacent to and around the eye but away from the user's nose, said body portion substantially entirely covering the eye when said body portion is in position on the user's face;
 said body portion includes an integral handle which is configured to be grasped between a thumb and a forefinger of the user, said integral handle forming a discontinuity in said peripheral edge that engages the user's face;
 said body portion defining an aperture for receiving a tip portion of the eye drop bottle; and
 said aperture being sized and positioned such that said tip portion of the eye drop bottle will be situated in a selected position spaced apart from said eye in which the drops are to be applied when said body portion is situated on and engaging the user's face.

2. A device as set forth in claim 1, further comprising a nose bridge extending from said body portion.

3. A device as set forth in claim 2, wherein said nose bridge comprises an arcuate member having a proximal end and a distal end, said proximal end being attached to said body portion.

4. A device as set forth in claim 1, wherein said aperture is defined by flexible fingers which frictionally engage said tip portion of said bottle in order to hold it in place.

5. A device as set forth in claim 1, wherein said aperture is defined by a flexible web.

6. A device as set forth in claim 3, wherein said aperture is located adjacent to said proximal end of said nose bridge.

7. A device as set forth in claim 6, wherein said aperture is located within a raised structure on said body portion.

* * * * *